(12) United States Patent
Gyrn

(10) Patent No.: US 8,246,588 B2
(45) Date of Patent: Aug. 21, 2012

(54) INSERTION DEVICE WITH PIVOTING ACTION

(75) Inventor: Steffen Gyrn, Ringsted (DK)

(73) Assignee: Unomedical A/S, Birkeroed (DK)

( * ) Notice: Subject to any disclaimer, the term of this patent is extended or adjusted under 35 U.S.C. 154(b) by 0 days.

(21) Appl. No.: 12/669,114

(22) PCT Filed: Jul. 3, 2008

(86) PCT No.: PCT/EP2008/058586
§ 371 (c)(1), (2), (4) Date: Apr. 21, 2010

(87) PCT Pub. No.: WO2009/010396
PCT Pub. Date: Jan. 22, 2009

(65) Prior Publication Data
US 2010/0204653 A1  Aug. 12, 2010

Related U.S. Application Data

(60) Provisional application No. 60/950,512, filed on Jul. 18, 2007.

(30) Foreign Application Priority Data

Jul. 18, 2007 (DK) .................................. 2007 01061

(51) Int. Cl.
*A61M 5/32* (2006.01)
*A61M 5/178* (2006.01)
*A61M 31/00* (2006.01)
*A61M 37/00* (2006.01)

(52) U.S. Cl. ................. 604/272; 604/164.08; 604/93.01

(58) Field of Classification Search .................. 101/334, 101/104; 604/164.08, 272, 93.01
See application file for complete search history.

(56) References Cited

U.S. PATENT DOCUMENTS 2,047,010 A  7/1936 Dickinson
(Continued)

FOREIGN PATENT DOCUMENTS

DE  4 342 329 A1  6/1994
(Continued)

OTHER PUBLICATIONS

International Search Report for International Application No. PCT/EP2008/058586 completed Oct. 6, 2008.
(Continued)

*Primary Examiner* — Christopher D Koharski
*Assistant Examiner* — Jenna Zhang
(74) *Attorney, Agent, or Firm* — Brinks Hofer Gilson & Lione

(57) ABSTRACT

The invention concerns an insertion device for inserting a medical device into the subcutaneous or intramuscular area of a patient. More specifically, this invention relates to an insertion device comprising pivoting and guiding means for moving a penetrating member from a position, where the penetrating member is not pointing into the direction of insertion, to a position, where the penetrating member is pointing into the direction of insertion. The inserter device comprises a housing (15) encompassing a penetrating member (9), said housing comprising a top section (14) and a lower section (16), wherein said insertion device (1) comprises pivoting means (27, 31, 41, 43) and guiding means (10, 19, 16*s*, 31*s*, 18*s*) providing one or more pivoting movement(s) of the penetrating member (9) from a first position, where the penetrating member (9) is not pointing into the direction of insertion, to a second position, where the penetrating member (9) is aligned with the direction of insertion, to a third position, where the penetrating member (9) protrudes the housing (15) and the penetrating member (9) is aligned in the direction of insertion. The guiding means (10, 19, 16*s*, 31*s*, 18*s*) are adapted to provide a longitudinal movement of the penetrating member (9) from the second to the third position.

23 Claims, 10 Drawing Sheets

U.S. PATENT DOCUMENTS

| | | |
|---|---|---|
| 2,295,849 A | 9/1942 | Kayden |
| 2,690,529 A | 9/1954 | Lindblad |
| 2,972,779 A | 2/1961 | Cowley |
| 3,074,541 A | 1/1963 | Roehr |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Pilger |
| 3,547,119 A | 12/1970 | Hall et al. |
| 3,610,240 A | 10/1971 | Harautuneian |
| 3,670,727 A | 6/1972 | Reiterman |
| 3,810,469 A | 5/1974 | Hurschman |
| 3,840,011 A | 10/1974 | Wright |
| 3,893,448 A | 7/1975 | Brantigan |
| 3,937,219 A | 2/1976 | Karakashian |
| 3,986,508 A | 10/1976 | Barrington |
| 3,995,518 A | 12/1976 | Spiroff |
| 4,022,205 A | 5/1977 | Tenczar |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,525,157 A | 6/1985 | Vaillancourt |
| 4,530,695 A | 7/1985 | Phillips et al. |
| 4,531,937 A | 7/1985 | Yates |
| 4,563,177 A | 1/1986 | Kamen |
| 4,610,469 A | 9/1986 | Wolff-Mooij |
| 4,617,019 A | 10/1986 | Fecht |
| 4,713,059 A | 12/1987 | Bickelhaupt et al. |
| 4,734,092 A | 3/1988 | Millerd |
| 4,755,173 A | 7/1988 | Konopka et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,970,954 A * | 11/1990 | Weir et al. .................... 101/334 |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olsen |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,248,301 A | 9/1993 | Koenig et al. |
| 5,256,149 A | 10/1993 | Banik et al. |
| 5,256,152 A | 10/1993 | Marks |
| 5,257,980 A | 11/1993 | Van Antwerp et al. |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,350,392 A | 9/1994 | Purcell et al. |
| 5,354,280 A | 10/1994 | Haber et al. |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,384,174 A | 1/1995 | Ward et al. |
| 5,387,197 A | 2/1995 | Smith et al. |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,490,841 A | 2/1996 | Landis |
| 5,501,675 A | 3/1996 | Erskine |
| 5,505,709 A | 4/1996 | Funderburk et al. |
| 5,507,730 A | 4/1996 | Haber et al. |
| 5,520,654 A | 5/1996 | Wahlberg |
| 5,522,803 A | 6/1996 | Teissen-Simony |
| 5,527,287 A | 6/1996 | Miskinyar et al. |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall |
| 5,643,216 A | 7/1997 | White |
| 5,643,220 A | 7/1997 | Cosme |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |

| | | |
|---|---|---|
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A * | 1/1999 | Tsals et al. .................. 604/135 |
| 5,865,806 A | 2/1999 | Howell |
| 5,899,886 A | 5/1999 | Cosme |
| 5,911,705 A | 6/1999 | Howell |
| 5,913,846 A | 6/1999 | Szabo |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rhinehart et al. |
| 5,951,523 A | 9/1999 | Osterlind et al. |
| 5,954,643 A | 9/1999 | VanAntwerp et al. |
| 5,957,892 A | 9/1999 | Thorne |
| 5,968,011 A | 10/1999 | Larsen et al. |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Peterson et al. |
| D417,733 S | 12/1999 | Howell et al. |
| 6,017,328 A | 1/2000 | Fischell et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stardella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,219,574 B1 | 4/2001 | Cormier et al. |
| 6,221,058 B1 | 4/2001 | Kao et al. |
| 6,248,093 B1 | 6/2001 | Moberg |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,379,335 B1 | 4/2002 | Rigon et al. |
| 6,387,076 B1 | 5/2002 | Van Lunduyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | R.o slashed.nborg et al. |
| 6,450,992 B1 | 9/2002 | Cassidy, Jr. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |
| 6,579,267 B2 | 6/2003 | Lynch et al. |
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Halseth et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,629,949 B1 | 10/2003 | Douglas |
| 6,645,182 B1 | 11/2003 | Szabo |
| 6,659,982 B2 | 12/2003 | Douglas et al. |
| 6,685,674 B2 | 2/2004 | Douglas et al. |
| 6,699,218 B2 | 3/2004 | Flaherty et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,749,587 B2 | 6/2004 | Flaherty |
| 6,749,589 B1 | 6/2004 | Douglas et al. |
| 6,776,775 B1 | 8/2004 | Mohammad |
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher |
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkinson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkenson et al. |
| 7,115,112 B2 | 10/2006 | Mogensen et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |

| | | |
|---|---|---|
| D554,253 S | 10/2007 | Kornerup |
| 7,303,543 B1 | 12/2007 | Maule et al. |
| 7,309,326 B2 | 12/2007 | Fangrow, Jr. |
| 7,407,491 B2 | 8/2008 | Fangrow, Jr. |
| 7,407,493 B2 | 8/2008 | Cane |
| 7,441,655 B1 | 10/2008 | Hoftman |
| 7,850,652 B2 * | 12/2010 | Liniger et al. ............ 604/164.08 |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2002/0022798 A1 | 2/2002 | Connelly et al. |
| 2002/0022855 A1 | 2/2002 | Bobroff et al. |
| 2002/0026152 A1 | 2/2002 | Bierman |
| 2002/0055711 A1 * | 5/2002 | Lavi et al. ...................... 604/110 |
| 2002/0068904 A1 | 6/2002 | Bierman et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Davis et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |
| 2004/0049159 A1 | 3/2004 | Barrus et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 * | 3/2005 | Vedrine ...................... 604/93.01 |
| 2005/0065472 A1 | 3/2005 | Cindrich et al. |
| 2005/0075606 A1 | 4/2005 | Botich et al. |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 * | 9/2005 | Kornerup et al. ............. 604/539 |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0015076 A1 | 1/2006 | Heinzerling et al. |
| 2006/0030815 A1 | 2/2006 | Csincsura et al. |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney, Jr. et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |

| | | | |
|---|---|---|---|
| 2007/0005017 A1 | 1/2007 | Alchas et al. | |
| 2007/0016129 A1 | 1/2007 | Liniger et al. | |
| 2007/0016159 A1 | 1/2007 | Sparholt et al. | |
| 2007/0021729 A1 | 1/2007 | Mogensen et al. | |
| 2007/0049865 A1 | 3/2007 | Radmer et al. | |
| 2007/0049870 A1 | 3/2007 | Gray et al. | |
| 2007/0066955 A1 | 3/2007 | Sparholt et al. | |
| 2007/0088271 A1 | 4/2007 | Richards et al. | |
| 2007/0093754 A1 | 4/2007 | Mogensen et al. | |
| 2007/0104596 A1 | 5/2007 | Preuthun et al. | |
| 2007/0112301 A1 | 5/2007 | Preuthun et al. | |
| 2007/0112303 A1 | 5/2007 | Liniger | |
| 2007/0129688 A1 | 6/2007 | Scheurer et al. | |
| 2007/0173767 A1 | 7/2007 | Lynch et al. | |
| 2007/0179444 A1 | 8/2007 | Causey et al. | |
| 2007/0185441 A1 | 8/2007 | Fangrow, Jr. | |
| 2007/0191772 A1 | 8/2007 | Wojcik | |
| 2007/0191773 A1 | 8/2007 | Wojcik | |
| 2007/0203454 A1 | 8/2007 | Shermer et al. | |
| 2007/0213673 A1 | 9/2007 | Douglas | |
| 2007/0244448 A1 | 10/2007 | Lastovich et al. | |
| 2008/0312601 A1 | 12/2008 | Cane | |
| 2010/0004597 A1 | 1/2010 | Gyrn et al. | |

FOREIGN PATENT DOCUMENTS

| | | |
|---|---|---|
| DE | 196 31 921 A1 | 3/1997 |
| DE | 299 05 072 U1 | 9/1999 |
| DE | 101 17 285 A1 | 11/2002 |
| DE | 203 20 207 U1 | 11/2004 |
| EP | 0117632 B1 | 9/1984 |
| EP | 0239244 B1 | 2/1987 |
| EP | 0451040 A1 | 10/1991 |
| EP | 0544837 B1 | 6/1993 |
| EP | 0615768 A2 | 9/1994 |
| EP | 0651662 B1 | 5/1995 |
| EP | 0657184 A1 | 6/1995 |
| EP | 0688232 B1 | 12/1995 |
| EP | 0714631 B1 | 6/1996 |
| EP | 0744183 A2 | 11/1996 |
| EP | 0747006 A1 | 12/1996 |
| EP | 0799626 A1 | 10/1997 |
| EP | 0937475 A2 | 8/1999 |
| EP | 0956879 A1 | 11/1999 |
| EP | 1086718 A1 | 3/2001 |
| EP | 1125593 A1 | 8/2001 |
| EP | 0775501 B1 | 6/2002 |
| EP | 1329233 B1 | 7/2003 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1475113 A1 | 11/2004 |
| EP | 1495775 A1 | 1/2005 |
| EP | 1 502 613 A | 2/2005 |
| EP | 1525873 A1 | 4/2005 |
| EP | 1527792 A1 | 5/2005 |
| EP | 1616594 A1 | 1/2006 |
| EP | 1704889 A1 | 9/2006 |
| EP | 1719537 A2 | 11/2006 |
| EP | 1762259 A1 | 3/2007 |
| FR | 2725902 A1 | 10/2004 |
| GB | 906574 | 9/1962 |
| GB | 2 088 215 A | 6/1982 |
| GB | 2 230 702 A | 10/1990 |
| GB | 2 423 267 A | 8/2006 |
| JP | 10179734 A | 8/1991 |
| JP | 7051251 A | 11/1995 |
| JP | 8187286 A | 7/1996 |
| JP | A-03-191965 A | 7/1998 |
| JP | 2002-028246 A | 1/2002 |
| WO | WO 81/01795 A1 | 7/1981 |
| WO | WO 82/03558 A1 | 10/1982 |
| WO | WO 92/04062 A1 | 3/1992 |
| WO | WO 93/05840 A2 | 4/1993 |
| WO | WO 96/32981 A1 | 7/1996 |
| WO | WO 96/20021 A1 | 10/1996 |
| WO | WO 98/58693 A1 | 12/1998 |
| WO | WO 99/07435 A1 | 2/1999 |
| WO | WO 99/33504 A1 | 7/1999 |
| WO | WO 00/02614 A1 | 1/2000 |
| WO | WO 00/03757 A1 | 1/2000 |
| WO | WO 00/44324 A1 | 8/2000 |
| WO | WO 01/30419 A2 | 5/2001 |
| WO | WO 01/68180 A1 | 9/2001 |
| WO | WO 01/72353 A2 | 10/2001 |
| WO | WO 01/76684 A1 | 10/2001 |
| WO | WO 01/93926 A2 | 12/2001 |
| WO | WO 02/02165 A2 | 1/2002 |
| WO | WO 02/07804 A1 | 1/2002 |
| WO | WO 02/40083 A2 | 5/2002 |
| WO | WO 02/053220 A2 | 7/2002 |
| WO | WO 02/081012 A2 | 10/2002 |
| WO | WO 02/081013 A2 | 10/2002 |
| WO | WO 02/083206 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 02/068014 A2 | 1/2003 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 2004/012796 A1 | 2/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/101016 A1 | 11/2004 |
| WO | WO 2004/101071 A2 | 11/2004 |
| WO | WO 2005/004973 A1 | 1/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/092410 A1 | 10/2005 |
| WO | WO 2005/094920 A1 | 10/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A1 | 6/2006 |
| WO | WO 2006/061354 A2 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/020090 A1 | 2/2007 |
| WO | WO 2007/065944 A1 | 6/2007 |
| WO | WO 2007/071255 A1 | 6/2007 |
| WO | WO 2007/071258 A1 | 6/2007 |
| WO | WO 2007/093182 A2 | 8/2007 |
| WO | WO 2007/140631 A1 | 12/2007 |
| WO | WO 2007/140783 A2 | 12/2007 |
| WO | WO 2007/140785 A1 | 12/2007 |
| WO | WO 2008/014791 A1 | 2/2008 |
| WO | WO 2008/014792 A1 | 2/2008 |
| WO | WO 2008/052545 A1 | 5/2008 |
| WO | WO 2008/065646 A1 | 6/2008 |
| WO | WO 2008/092782 A1 | 8/2008 |
| WO | WO 2008/092958 A2 | 8/2008 |
| WO | WO 2008/092959 A1 | 8/2008 |
| WO | WO 2008/135098 A1 | 11/2008 |

| | | |
|---|---|---|
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010399 A1 | 1/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2010/072664 A1 | 7/2010 |
| WO | WO 2010/112521 A1 | 10/2010 |

OTHER PUBLICATIONS

International Preliminary Report on Patentability for International Application No. PCT/EP2008/058586 completed Oct. 15, 2009.
"Why inset®?" inset® infusion set product overview; http://web.archive.org/web/20040906102448/http://www.infusion-set.com/Default.asp?ID=108; two pages.

* cited by examiner

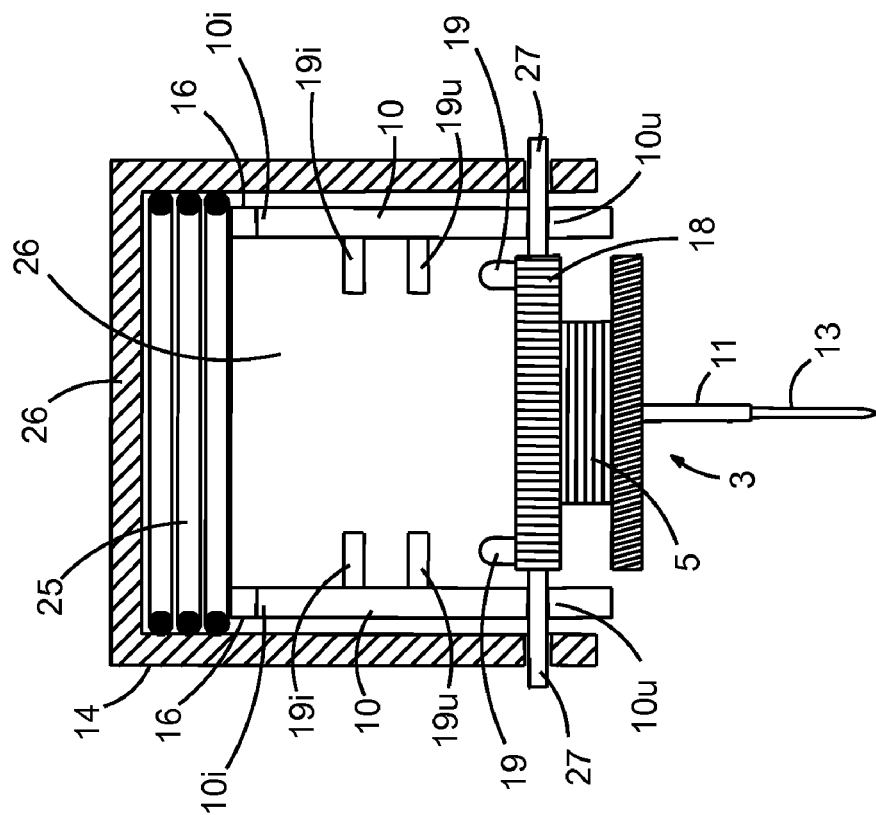
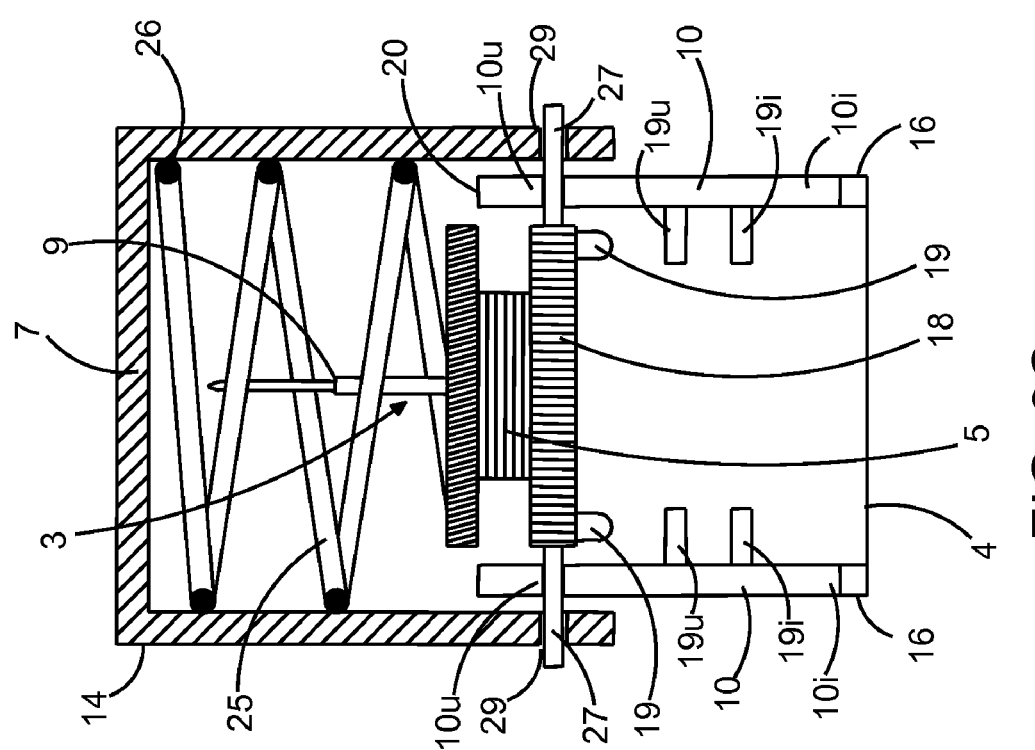

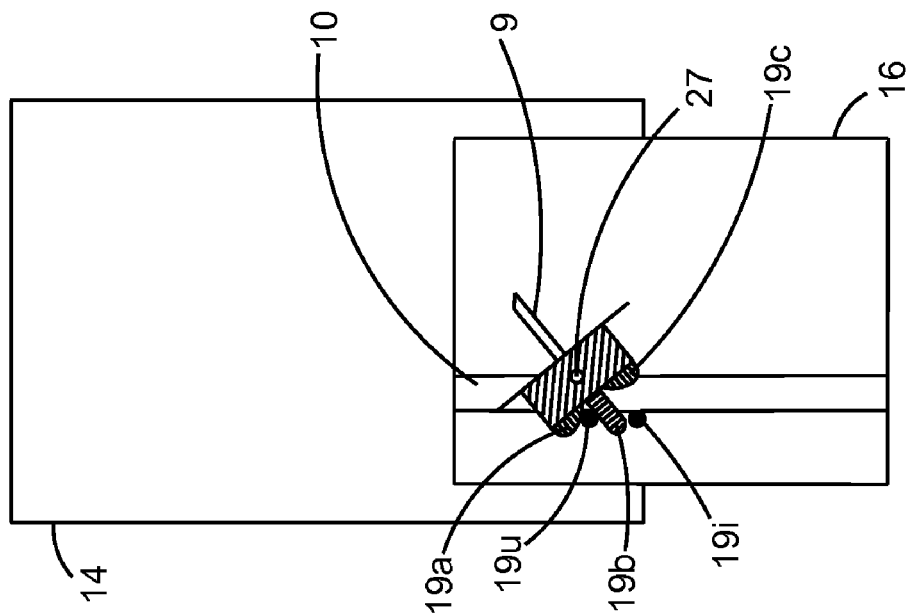
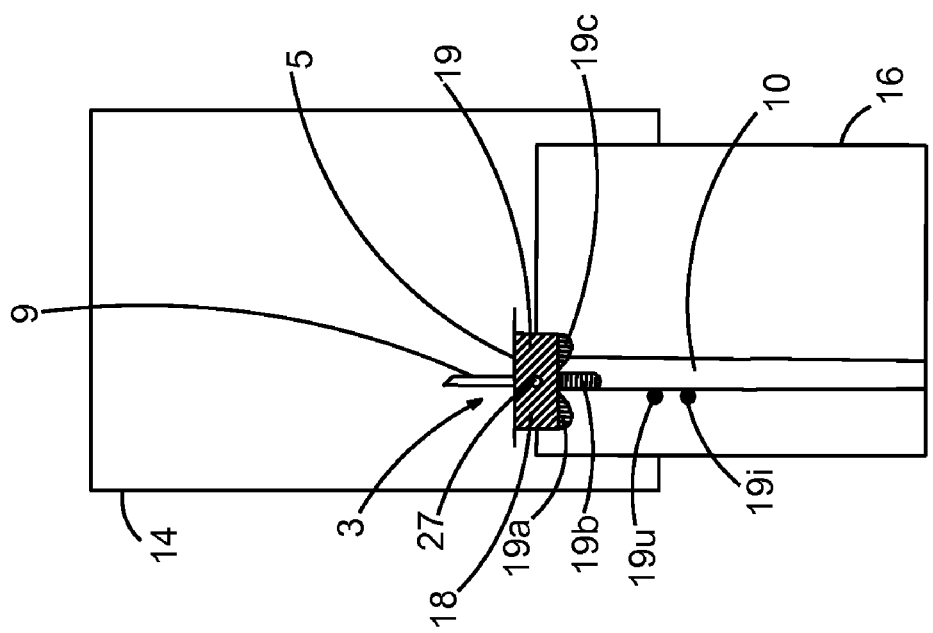

INSERTION DEVICE WITH PIVOTING ACTION

This application claims the benefit under 35 U.S.C. §371 of International Application No. PCT/EP2008/058586, filed Jul. 3, 2008, which claims the benefit of Danish Application No. PA 2007 01061 filed Jul. 18, 2007 and U.S. Provisional Application Ser. No. 60/950,512, filed Jul. 18, 2007, the entirety of which are incorporated herein by reference.

TECHNICAL FIELD OF THE INVENTION

The invention concerns an insertion device for inserting a medical device into the subcutaneous or intramuscular area of a patient. More specifically, this invention relates to an insertion device comprising pivoting and guiding means for moving a penetrating member from a position, where the penetrating member is not pointing into the direction of insertion, to a position, where the penetrating member is pointing into the direction of insertion.

BACKGROUND OF THE INVENTION

Insertion devices, also called injectors, are commonly used in the medical field for inserting medical devices such as infusion sets and the like, in a semi-automated fashion through the skin of a patient.

EP 1 011 785 relates to an injector for a subcutaneous infusion set, EP 1 044 028 concerns an insertion device for an insertion set.

EP 1 502 613 relates to an inserter device for inserting a penetrating member into the subcutaneous area of a patient. The penetrating member according to this inserter device performs a curved movement during the insertion i.e. the penetrating member continuously changes direction even after the point of the penetrating member has penetrated the skin surface of the patient. This curved movement can cause discomfort or even pain to the patient.

It is known that any patients, especially children, are afraid of sharp objects, such as injection needles and other penetrating devices, commonly used for medical treatment and therapy. This fear is often irrational, and it may hamper an appropriate medical treatment. For example in the case of self-medication, a lack of administration of an appropriate dose of a required medical composition can lead to complications, which may even be life-threatening. When treating diabetes, e.g. in juveniles, there is a risk that the required insulin-dose may not be self-administered due to irrational fear of the device's needle, combined with a general lack of knowledge and awareness concerning the consequences of omitting the correct application of the device and dosage.

A further known issue with insertion of medical devices is the risk of contamination of the penetrating member before or during application. This can easily lead to the introduction of an infection to a patient, e.g. through a contaminated insertion needle. The longer such a needle is exposed, the higher the risk of accidental contamination, e.g. by touching the needle with a finger, bringing the needle in contact with an unclean surface, or by airborne contamination, aerosol contamination and the like. Depending on the nature of the contamination (e.g. comprising virus, bacteria, fungus, yeast and/or prion) combined with the general health status of the patient, the resulting infection can rapidly turn into a life threatening situation.

Finally, it is well known that contact with an infected, used needle especially in hospital environments can be life-threatening, and the risk of accidental exposure to contaminated material must be minimized.

Thus, there is an obvious need in the art for a robust, reliable, accurate, safe, and user friendly insertion device, which addresses the issues discussed above.

SUMMARY OF THE INVENTION

The current invention provides an insertion device, where the penetrating device, such as needle or cannula or both, are not visible prior, during and after insertion of the medical device, whereby administration and handling is drastically facilitated, and user friendliness is improved. Further this device reduces the risk of infections and contaminations, due to the absence of an exposed penetrating device. When applicable, the medical device's insertion needle is retracted into the housing of the insertion device, thus facilitating handling and disposing of the medical device in question.

Thus, the present invention provides an insertion device as defined by claim 1 for inserting a penetrating member into the subcutaneous area and/or intramuscular area of a patient, said inserter device comprising a housing encompassing the penetrating member, which housing further comprises a top section and a lower section. The insertion device also comprises pivoting means and guiding means for providing one or more pivoting movement(s) and one or more longitudinal movement(s) of the penetrating member from a first position, where the penetrating member is not pointing into the direction of insertion, to a second position, where the penetrating member is aligned with the direction of insertion but not protruding said housing, to a third position, where the penetrating member protrudes the housing and the penetrating member is aligned in the direction of insertion.

The pivoting and guiding means can also provide a fourth position by a longitudinal movement in which position the penetrating element is fully inserted in the patient, where the longitudinal movement being of the same length or longer than the length of the penetrating member.

According to one embodiment the pivoting means comprise one or more shafts. This shaft can traverse the top section and/or the lower section. E.g. the shaft can consists of one through-going member or the shaft can consists of two or more pieces.

According to one embodiment the device mounting means, on which the medical device are attached, are attached to said shaft, and the device mounting means and the shaft share the same center of rotation.

According to one embodiment the pivoting means comprise one or more pivoting shafts and one or more pivoting members. E.g. a first pivoting shaft can traverse the lower section and a pivoting member, and the first pivoting shaft is the centre of rotating of said pivoting member. Further a second pivoting shaft can traverse the pivoting member and the device mounting means.

According to one embodiment the guiding means comprise one or more guiding slots. These guiding slots can be provided on the lower section where the guiding slots can be parallel to the direction of insertion, and are of the same length or longer than the length of said longitudinal movement. The guiding slots can be encompassing the shaft, and restrict the length of the longitudinal movement of the shaft and the lower section.

The guiding slot can be provided within a pivoting member, where the guiding slot comprises a bend section towards the upper part of the pivoting member, and a straight section of the same length or longer than the length of said longitudinal movement. The guiding slot encompasses and restricts the movement of said shaft.

The guiding slot can be provided within a vertical section of the device mounting means. The guiding slot is then of the same length or longer than the length of said longitudinal movement, and the guiding slot encompasses the second pivoting shaft, and restricts the movement of the second pivoting shaft.

According to one embodiment the application of a downward force on the top section into the direction of insertion provides a rotation of the medical device through interactions of the shaft being guided by the guiding slot of the lower section and the guiding slot of the pivoting member, and through interactions of the first and second pivoting shafts being guided by the pivoting member and guiding slot on the vertical section of the device mounting means.

According to one embodiment the guiding means comprise one or more rounded protrusions provided on the device mounting means, said protrusions extending away from the direction of insertion. The guiding means comprise a major protrusion flanked symmetrically by two minor protrusions, where the major protrusion is aligned with the penetrating member along an axis perpendicularly to the shaft. According to this embodiment the device can comprise upper guiding means and lower guiding means, where the upper and lower guiding means are extending from the inner surface of the lower section. Upon application of a downward force on the top section the interaction between the protrusions and the upper and lower guiding means provides a rotation of the medical device.

According to one embodiment the penetrating member comprises a cannula and/or an introducer needle. If the introducer needle is part of the inserter device, then the introducer needle is removed from the medical device after insertion of the penetrating member.

According to one embodiment the pivoting and guiding means can provide a fifth position by a longitudinal movement, optionally accompanied by a pivoting or rotational movement, where the introducer needle is retracted through the cannula. This fifth position can be provided by one or more linear movements and one or more pivoting movements, where the needle is retracted into the housing. The device can be constructed in a way where the introducer needle is no longer visible after retraction into the housing.

According to one embodiment the penetrating member is a part of a medical device e.g. the penetrating member consist of a hard penetrating cannula.

According to the invention the medical device can be a sensor, or an infusion part, or a gateway/port for injection of a fluid.

According to the invention the inserter device can either be for single use (disposable) or be suitable for repeated use e.g. depending on the materials used to construct the device.

According to the invention the inserter device can be suitable for inserting different medical devices, either simultaneously or consecutively.

According to the invention the inserter device can be cleaned, disinfected and/or sterilized before, after or in between uses.

According to the invention the inserter device can comprise a penetration member which is "in center" or "off center" of the inserter device.

According to the invention the inserter device can comprise additional cover and/or protection means.

According to the invention the inserter device can have a central axis of insertion which is parallel to the central axis of the insertion device.

According to the invention the inserter device can have a central direction of insertion of the penetrating member which is either essentially perpendicular to the patient's skin, i.e. has an insertion angle $\alpha_{ins}$ around 90°, or have an insertion angle $0°<\alpha_{ins}<90°$, or $10°<\alpha_{ins}<80°$, or $20°<\alpha_{ins}<70°$.

According to the invention the inserter device can have a center axis of the inserter device which is essentially perpendicular to the patient's skin, i.e. has a center axis angle $\alpha_{center}$ around 90°, or at an center axis angle $0°<\alpha_{center}<90°$, or $10°<\alpha_{center}<80°$, or $30°<\alpha_{center}<60°$.

According to the invention the inserter device can have a direction of insertion of the penetrating member which is either parallel to the center axis of the inserter device, i.e. has a deflection angle $\alpha_{defl}=0°$, or has a deflection angle $0°<\alpha_{defl}<90°$, or $10°<\alpha_{defl}<80°$, or $30°<\alpha_{defl}<60°$.

BRIEF DESCRIPTION OF THE DRAWINGS

A detailed description of embodiments of the current invention will be made with reference to the accompanying figures, wherein like numerals may designate corresponding parts in different figures.

DETAILED DESCRIPTION OF THE INVENTION

Figure 1:
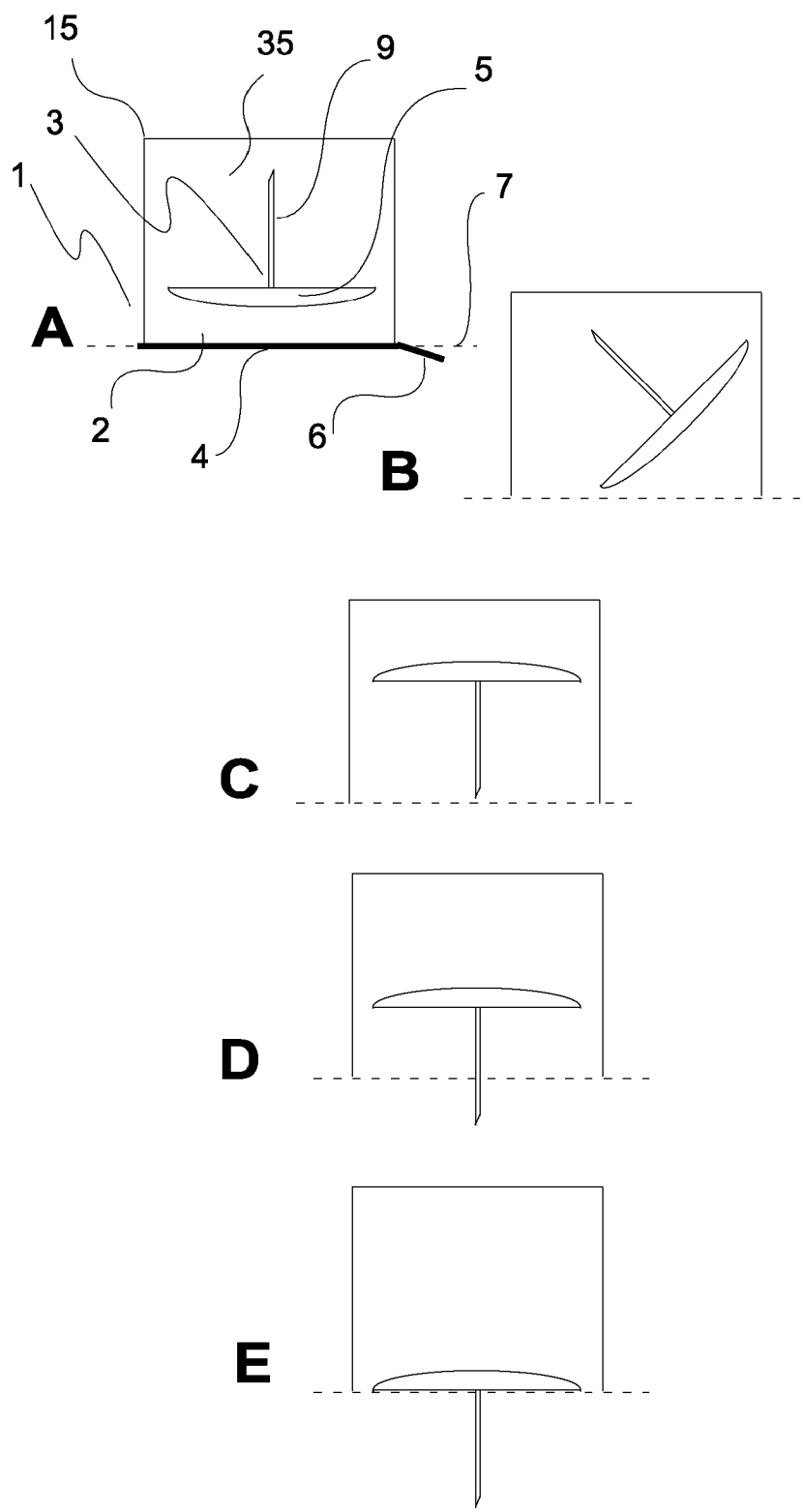
FIG. 1: Schematic representation of different positions of a medical device within an insertion device.

FIG. 1 shows an insertion device 1, and illustrates different positions of a medical device 3 within the main cavity 35 of the insertion device 1; said medical device 3 comprises a penetrating member 9, according to the current invention. The main cavity 35 is defined as the volume within the housing 15 of the insertion device 1 and a bottom plane 7, illustrated by a stippled line. The main cavity 35 is sufficiently dimensioned, in width, height and diameter, and optionally flexible and/or variable in size to encompass a medical device 3 comprising a penetrating member 9, and to allow for one or more rotations and/or pivoting movement, and optionally, one or more longitudinal movements (FIG. 1).

The insertion device according to the invention comprises an opening 2 towards the bottom plane 7 of the housing 15. Said opening is as wide as, or wider than the body 5 of the medical device 3 to be inserted. The embodiment of an insertion device 1 shown in FIG. 1 comprises an opening 2, which is sufficiently wide to allow the medical device 3 to leave the insertion device 1 through said opening 2. Often, the opening 2 can be sealed with a detachable sealing foil or release liner, which can comprise a flap 6 in order to facilitate the removal process before use of the insertion device. This may ensure an appropriate hygiene standard, such as maintaining appropriate levels of disinfection or sterility. Furthermore, the sealing foil may act as an indicator for integrity of the insertion device 1 and/or medical device 3, thereby improving safety standards, as use of potentially compromised and thus no longer sterile device can be avoided.

In the start position according to the embodiment of the invention depicted in FIG. 1A, the penetrating member 9 of the medical device 3 is turned 180° away from the direction of insertion. The direction of insertion being equivalent to 0° is in this example perpendicular to the bottom plane 7. In this case the penetrating member 9 is pointing upwards, as depicted in FIG. 1 (position A). The penetrating member 9 is not visible in position A when looking into the main cavity 35, as the penetrating member 9 is shielded by the body 5 of the medical device no matter how small the body 5 of the medical device is. In another embodiment, the medical device is turned away from the direction of insertion at an angle of around 135° in the start position. In a further embodiment, the medical device is turned away from the direction of insertion at an angle between >0° and 180°, and the insertion device is not visible and/or shielded by the housing 15 and/or the body 5 of the medical device 3.

According to the invention, the insertion device comprises pivoting and guiding means for providing a $2^{nd}$ position, position C, at this position the medical device 3—including the penetrating member 9—is still within the main cavity 35, thus not protruding the insertion device 1, and the medical device and the penetrating member 9 are aligned in the direction of insertion (FIG. 1).

Via a $3^{rd}$ position, position D, where at least a part of the penetrating member 9 protrudes the housing 15, the insertion device arrives at a $4^{th}$ position, position E, where the penetrating member 9 is fully extended. This extending of the penetrating member 9 is achieved by an essentially longitudinal movement in the direction of insertion, which is at least as long as the length of the penetrating member 9 as the penetrating member 9 has to be inserted in full length.

Figure 2:
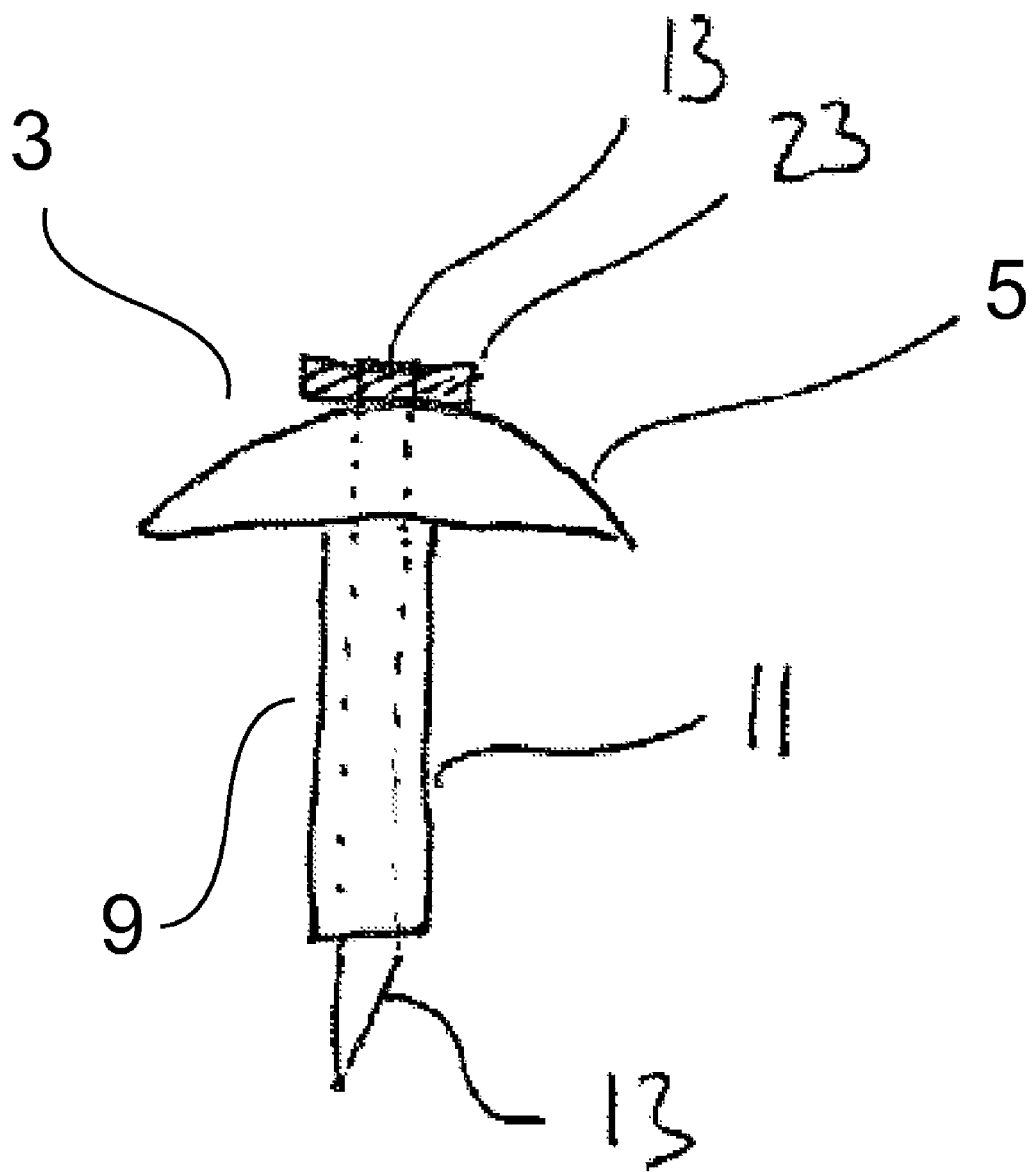
FIG. 2: Schematic representation of a medical device which can be inserted with the insertion device.

FIG. 2 illustrates an embodiment of a medical device 3 which can be inserted with an inserter device according to the invention. Commonly, such a medical device 3 comprises a body 5, which is not inserted into the patient but rests on the patient's skin, and one or more penetrating members 9. The medical device depicted in FIG. 2 is a port device set possessing a penetrating member 9 comprising a soft cannula 11 and an introducer needle 13. In case of a soft cannula, which cannot be inserted without aid of e.g. an insertion needle, the insertion needle is retracted upon application of the medical device. This may require attachment means 23 for manual retraction of the introducer needle 13, which are also shown in FIG. 2. Other medical devices may comprise a cannula with penetrating ability which remains inserted in the patient upon application of the medical device.

Medical devices that can be inserted according to the invention comprise e.g. infusion sets or the infusion part of an infusion set, sensor devices comprising one or more inserted sensors, port devices which only comprises a body with a restricted access for replacing repeated injections with syringes or any other device which has a penetrating member inserted into the subcutaneous area or intramuscular area of a patient Often, a mounting pad is used to ensure the appropriate contact of the medical device with the skin of the patient. This mounting pad may be attached to the underside of the body 5 of the medical device 3. Alternatively, the mounting pad is attached to the skin of the patient, and the medical device is inserted directly through the mounting pad, or through an opening in the mounting pad. Generally, the mounting pad's adhesive strength is sufficiently strong to ensure that the medical device remains on the skin of the patient after insertion, and only the insertion needle 13 is removed through the cannula 11, while the medical device remains in place. In an alternative embodiment of the current invention, the medical device 3 is inserted through a second medical device.

Figure 3B:
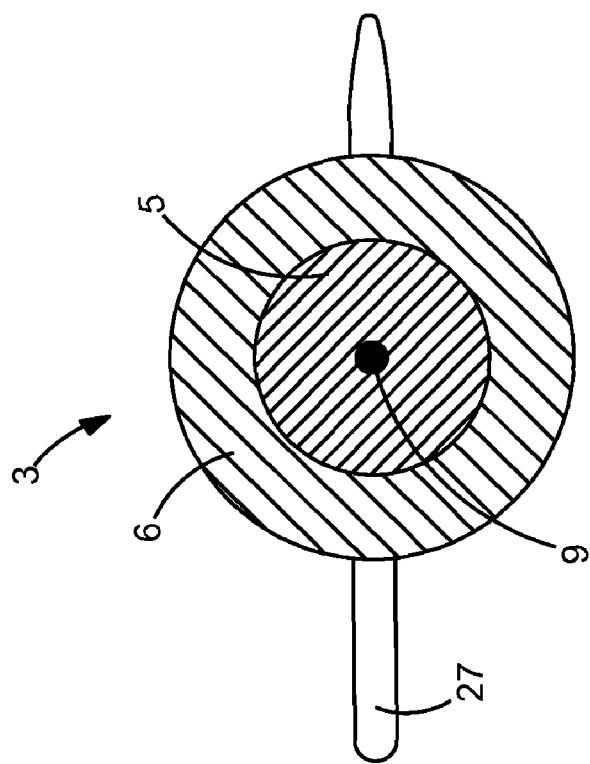
FIG. 3: Schematic representation of an insertion device.
Figure 3A:
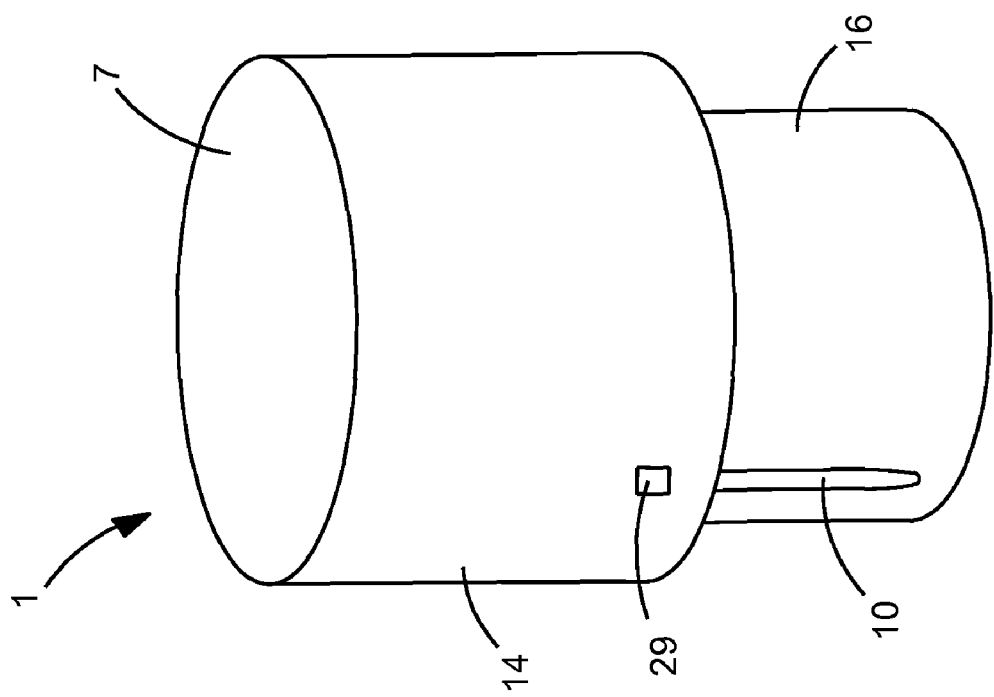

FIG. 3 depicts a further embodiment of the invention. FIG. 3A shows a housing of an insertion device according to the invention. The housing of the insertion device 1 comprises to sections, a top section 14 and a lower section 16, both essentially in the shape of a hollow cylinder jacket; the two sections can have any cross-section e.g. cylindrical as shown in FIG. 3, or elliptic or polygonal e.g. square as long as the top section 14 and the lower section 16 corresponds to each other. Top section 14 is closed at the top via a top surface 7. The diameter of the top part 15 is wider than the diameter of the lower section 16, and the two sections are about similar in height, and the top section 14 overlaps the lower section 16.

Towards the lower part of top section 14, attachment means 29 comprising a through-going hole and optionally a bearing are provided for attaching rotating/pivoting means. The rotating/pivoting means comprises a cylindrical aperture or bearing for a rotating/pivoting shaft 27, which is mounted within the top section 14. The attachment means 29 are situated symmetrically, and optionally diametrically.

The lower section 16 is neither closed at the top or at the bottom, and comprises a pair of symmetrical guiding slots 10 positioned vertically, i.e. parallel to the direction of insertion and symmetrically across a diagonal line across the lower section 16. The guiding slot 10 is dimensioned sufficiently wide to provide guiding of the rotating/pivoting shaft 27 and to allow a longitudinal movement of the rotating/pivoting shaft 27 along the guiding slot 10. Top section 14 and lower section 16 are connected via said rotating/pivoting shaft 27.

FIG. 3B shows a top view of a medical device 3 with the penetrating member 9 pointing towards the observer. The proximal side of the body 5, i.e. the side facing the skin of the patient, upon application of the medical device 3 is seen, as well as a mounting pad 6. The ends of the pivoting/rotating shaft 27 that are protruding the mounting pad 6 are visible.

FIG. 3C shows a view of a cross section along or parallel to the pivoting/rotating shaft 27 of the insertion device 1, whereby further constituents and features become apparent. The penetrating member 9 of the medical device 3 is pointing up (i.e. position 1, FIG. 1) towards the closed circular top surface 7 of the top section 14. The medical device 3 is attached in a releasable fashion to a pivoting/rotating shaft 27 via device mounting means 18. According to one embodiment of the invention, medical device 3 is attached to the device mounting means 18 via the introducer needle 13 and the friction between said introducer needle 13 and the cannula 11. The introducer needle 13 is retracted upon insertion of the medical device 3. The friction between introducer needle 13 and cannula 9 provides sufficient and appropriate attachment between the device mounting means 18 and the medical device 3 before and during insertion. Sufficient and appropriate attachment means that the medical device 3 does not e.g. slide off or fall off the device mounting means 18 or introducer needle 13 unintendedly—such as before application (including production, sterilization, transport and storage) or during application, which includes the centrifugal force(s) that are induced by the one or more rotational and/or pivoting movements during insertion. Sufficient and appropriate attachment means also, that the friction is not too high, allowing for retraction of the penetrating needle 13 after insertion. Thus the dimensions of the outer diameter of the introducer needle 13 and the inner diameter of the cannula 9, as well as their surface properties are dimensioned and selected accordingly. According to another embodiment of the invention, the medical device 3 is attached to the device mounting means 18 and/or pivoting/rotating shaft 27 via adhesive means. The function of the adhesive means is to provide sufficient and appropriate attachment/adhesion between the medical device 3 and the device mounting means and/or pivoting/rotating shaft 27 that the medical device remains securely attached before and during insertion, but allowing release of the medical device 3 upon insertion. The adhesive means are selected and dimensioned accordingly.

A cross section of the device mounting means 18 is shown in FIG. 3C. The pivoting/rotating shaft 27 is either extending through the device mounting means 18, or two independent pivoting/rotating shafts 27 are mounted symmetrically and aligned in the same pivoting/rotating axis on each side of the device mounting means 18. A pair of guiding means 19 is attached on the opposite face of the device mounting means 18, that is, with respect to the medical device, the face pointing 180° away from the direction of insertion of the penetrating member 9. The guiding means 19 are positioned symmetrically towards the outer extremity of the device mounting means, and their distance exceeds the diameter of the medical device 3. In position 1, the pivoting/rotating shaft 27 is parallel to the top section's 14 top surface 7 as well as to the lower section's 16 opening 2, which in this embodiment is closed by a sealing device 4. In an alternative embodiment of the invention, the sealing device may be a mounting pad. In the depicted embodiment, the guiding slot 10 extends across approximately ⅔ of the height of the lower section 16. Alternatively, the guiding slot 10 can of similar length as the length of the penetrating member 9 or longer. The guiding slot 10 has an upper 10*u* and a lower end 10*l*. The pivoting/rotating shaft 27 extends through the guiding slot 10 and through the opening 29 of the top section 14. The height of the top section 14 and lower section 16 exceed each the length of the medical device 3.

Upper guiding means 19*u* and lower guiding means 19*l* are provided, which extend perpendicularly from the inner surface of the lower section 16, and essentially parallel to the top surface 7. In one embodiment of the invention, upper and lower guiding means 19*u* and 19*l* are cylindrical. In another embodiment of the invention, upper and lower guiding means 19*u* and 19*l* are essentially elliptical in diameter. In a further embodiment, and lower guiding means 19*u* and 19*l* have a square diameter, optionally with rounded edges. Upper and lower guiding means 19*u* and 19*l* are positioned below the device mounting means and guiding means 19, when the medical device 3 is in position 1. The length of the upper and lower guiding means 19*u*, 19*l* is sufficient to enable contact with the guiding means 19 upon lowering the device mounting means. A helical spring 25 having a diameter of approximately the outer diameter of the lower section 14, is placed between on the inside of the top section 16 and the lower section 14. The helical spring 25 may be attached to the inner surface of the top section 16 and/or the circular top surface 7. Furthermore, the helical spring 25 may rest and/or be attached to a distal surface, e.g. the top surface 20 of the wall of the lower section 14. When the insertion device is in position 1, the helical spring 25 is in an essentially relaxed state, or close to a relaxed state. The action of the helical spring 25 provides a close to maximal separation of top and lower sections 14, 16, combined with a near maximal volume of their combined cavities, and maintains the medical device in a position, with the penetrating member 9 pointing upwards, i.e. position 1 according to FIG. 1.

FIG. 3D shows the insertion device in a fully inserted position corresponding to the 4<sup>th</sup> position is seen in FIG. 1E, where the medical device 3 has rotated 180°, the penetrating member 9 and body 5 protrude top and lower sections 14, 16, and the penetrating member 9 will be fully inserted when the insertion device is placed close against the patients skin. When applying a force, e.g. by applying a pressure on the top section 14 in the direction of insertion against the lower section 16, the helical spring 25 will be energized and compressed between the top surface 7 and the top surface 20 of the wall of the lower section 16. The top and lower sections 14, 16 have been set in motion towards each other, thus minimizing the volume of the main cavity 35. The rotating/pivoting shaft(s) 27—onto which the device holding means comprising guiding means 19 are attached—has moved down the lower end 10*l* of guiding slot 10, in the direction of insertion of the device, and has passed the upper and lower guiding means 19*u*, 19*l*. The consecutive or combined actions and interactions of the guiding means 19, 19*u*, 19*l* and rotating/pivoting means 27, 18, 29, combined with a forward motion, have provided a pivoting/rotation of the medical device 3 of approximately 180°, combined with a longitudinal movement. Consequently, the guiding means 19 are now below the upper and lower guiding means 19*u*, 19*l*. As depicted in the embodiment presented in FIG. 3D, the guiding means 19—situated on the device mounting means 18—and 19*l* are in contact with each other.

Helical spring 25 is selected and dimensioned according to its function. One function of the helical spring 25 is to provide sufficient energy to separate top section 14 and lower sections 16 after insertion of the penetrating member 9 of the medical device 3. According to one embodiment of the invention, the helical spring 25 provides sufficient energy to separate the medical device 3 from the insertion device after insertion, and optionally to return the device mounting means 18 and pivoting/rotating shaft 27 back into the start position, or into a position close to the start position, such as positions A and B in FIG. 1. According to another embodiment of the invention, the helical spring 25 provides also sufficient energy to retract penetrating needle 13 after insertion into a patient.

FIG. 4 shows a view of a longitudinal cross section perpendicular to the pivoting/rotating shaft 27. FIG. 4 illustrates a similar embodiment as shown in FIG. 3 but from an angle perpendicular to the view angle of FIG. 3. In FIG. 4 the abovementioned actions and interactions of the respective guiding and pivoting/rotating means are shown in more details.

The insertion device 1 comprises an top section 14 and a lower section 16, where the top section 14 is wider than the lower section 16, and the top section 14 overlaps at least in part the lower section 16. Their shape (cross-section perpendicular to the longitudinal axis of the insertion device may be cylindrical, elliptical, rectangular, or comprise a combination of round and linear profiles). In one embodiment of the invention, the cross section is rotational-symmetrical, or symmetrical across at least one diagonal line, such as mirror symmetrical (not shown).

FIG. 4 shows essentially the same features as FIG. 3. However, in this embodiment, the device mounting means 18 comprise guiding means 19, which comprise three distinct, rounded protrusions: a first protrusion 19*a*, a second protrusion 19*b* and a third protrusion 19*c*. The second protrusion 19*b* is more elongated than the first protrusion 19*a* and the third protrusion 19*c*, and is flanked by the first and the third protrusions 19*a* and 19*c*. The third protrusion 19*a* and the third protrusion 19*c* are positioned symmetrically around the second protrusion 19*b*, with protrusion 19*b* in the centre. The centre line of the second protrusion 19*b* is essentially aligned along an axis being perpendicular to and going through the rotating/pivoting shaft 27 and being aligned with the penetrating member 9. Said axis is also the axis of symmetry for the first and the third protrusions 19*a* and 19*c*.

FIG. 4A shows the penetrating member 9 of the medical device 3 in a 1st position where it is pointing upwards, deflected 180° from the direction of insertion. The pivoting/rotating shaft 27 is positioned at the upper end 10u of the guiding slot 10. The guiding means 19u and 19l are not in contact with the protrusions 19a, 19b or 19c.

FIG. 4B shows the penetrating member 9 of the medical device 3 in a position where it is pointing approximately 135° away from the insertion direction. This position is achieved when applying a downward force onto the top section 14, thereby guiding the pivoting/rotating axis 27 into the direction of insertion, and combining this forward movement with a pivoting, sideward guiding providing a rotating movement (clockwise) of approximately 20°-70°, or around 45°. The pivoting/rotating axis 27 has moved downwards along the guiding means 10, and is now positioned around the upper third of the guiding means 10. The central protrusion 19b is now interacting and/or in contact with guiding means 19u and is located in between guiding means 19u and guiding means 19l. Both protrusion 19a and 19b are interacting and/or in contact with guiding means 19u, which is located in between protrusion 19a and 19b.

Figure 4D:
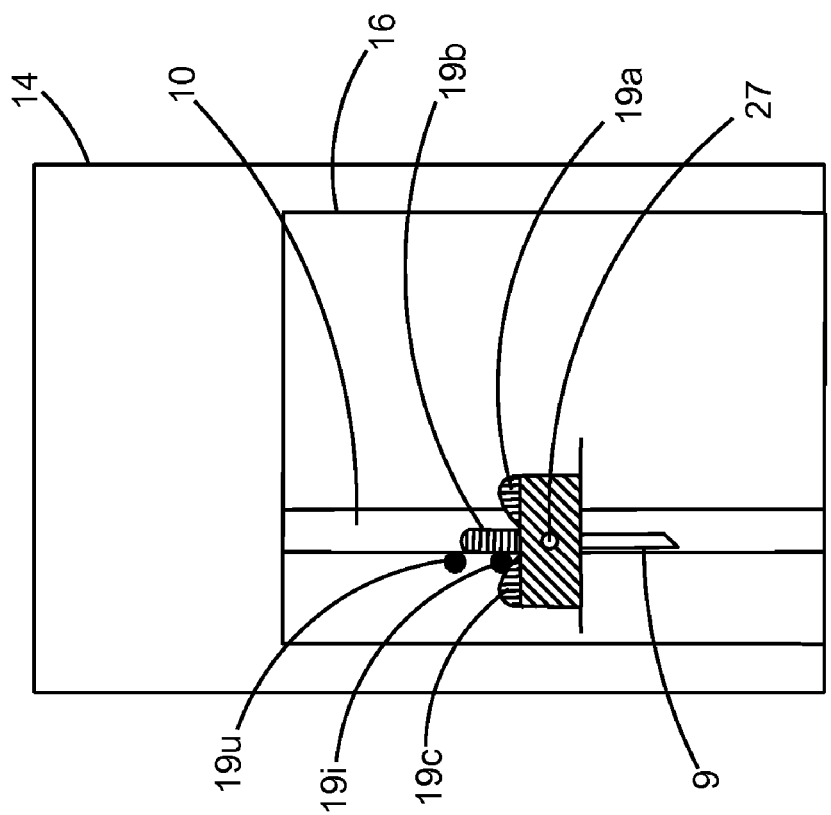
FIG. 4: Schematic representation of an insertion device.
Figure 4C:
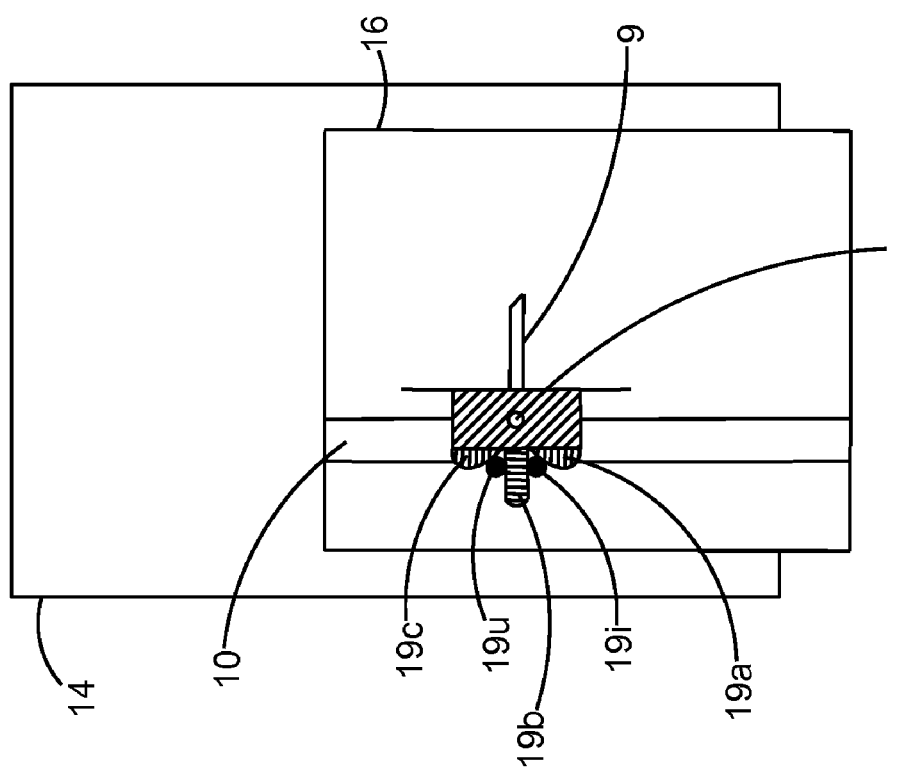

FIG. 4C illustrates that a further downward force as described above leads to the medical device 3 and device mounting means 18 being pivoted/rotated approximately 90°. In this position, the guiding means 19u and 19l are interacting with the protrusions 19a, b and c. It becomes apparent that the distance between guiding means 19u and 19l is preferably the same or larger than the width of the protrusion 19b. Likewise, the distances between protrusion 19a and protrusion 19b, as well as the distance between protrusion 19b and protrusion 19c are preferably the same or larger than the diameter of the guiding means 19u and guiding means 19l, respectively.

FIG. 4D shows that a further downwards force as described above leads to a further pivoting/rotational movement by the action and interaction of the above described guiding means 19u and 19l in combination with the protrusions 19a, b and c. The rotation stops when the penetrating means are aligned with the direction of insertion, which in the depicted embodiment is after a rotation/pivoting movement of a further 90°, so that the total rotation/pivoting movement is 180°. The final 90° turn is achieved by the interaction of the large protrusion 19b and minor protrusion 19c and the groove between said protrusions with the lower guiding means 19l. As illustrated, a further downwards force in the direction of insertion will lead to a longitudinal insertion of the penetrating member in the desired insertion direction. The length of the longitudinal insertion movement is controlled by the applied downwards force, and the length of the guiding slot 10, where the bottom section of the guiding slot 10l is determining the remaining length of insertion, optionally combined with alternative means (not shown and not described).

Figure 5:
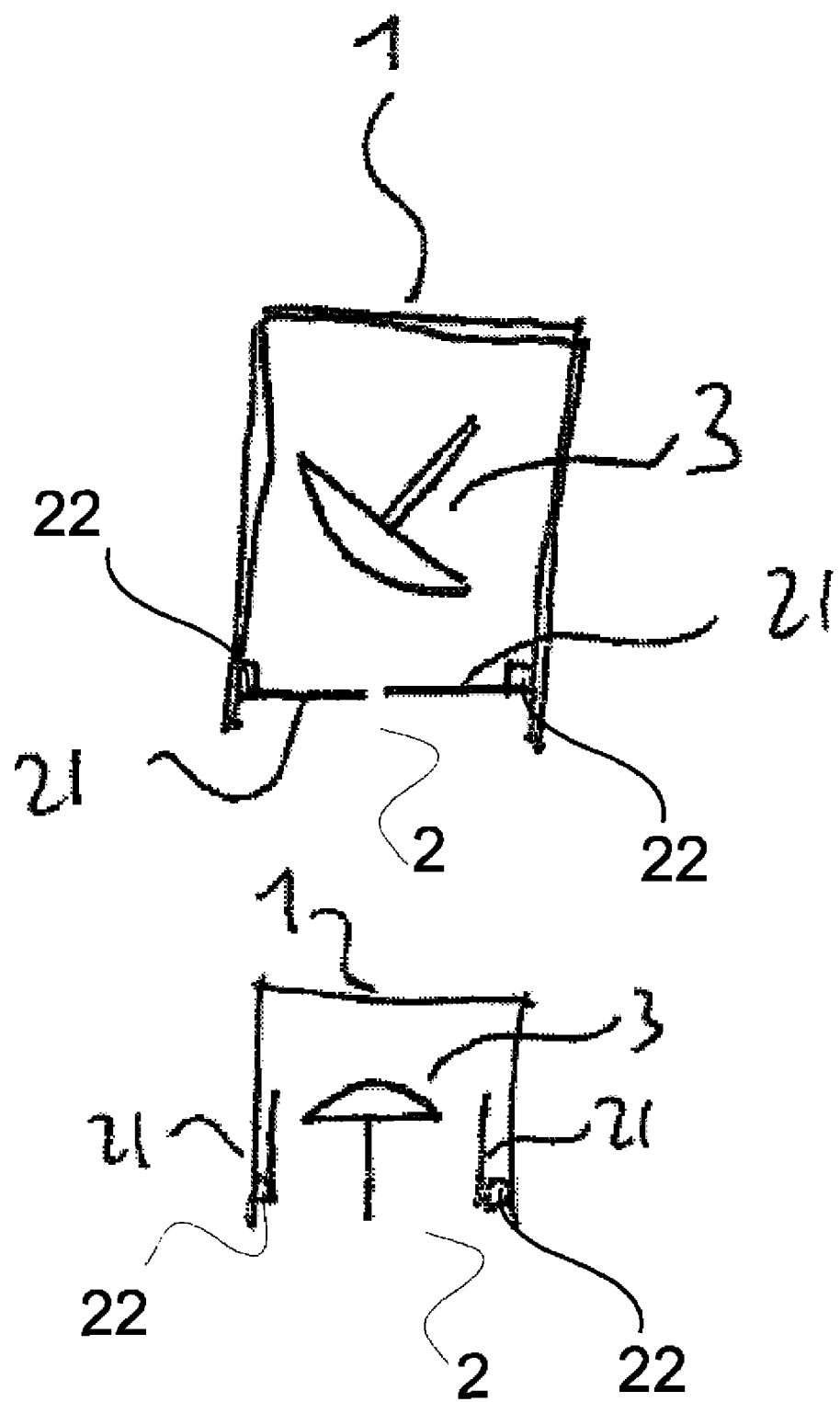
FIG. 5: Schematic representation of an insertion device with shielding means.

FIG. 5 illustrates means for protecting and shielding the medical device 3 and its penetrating member 9 from being visible and accessibility. One or more protection means 21 are attached to the inner surface of the insertion device 1 by attachment means 22. Upon activating the insertion device 1, i.e. in the process of insertion of a medical device 3, the protection means 21 are moved from a position, where they are shielding the opening 2 to a position, where they allow passage of the medical device 3. This movement may comprise one or more longitudinal, rotational or pivoting movements, either consecutively or simultaneously or in an overlapping fashion. The required activation means are not shown. In FIG. 5 B, the protection means 21 are pivoted upwards, allowing passage of the medical device 3.

Figure 6:
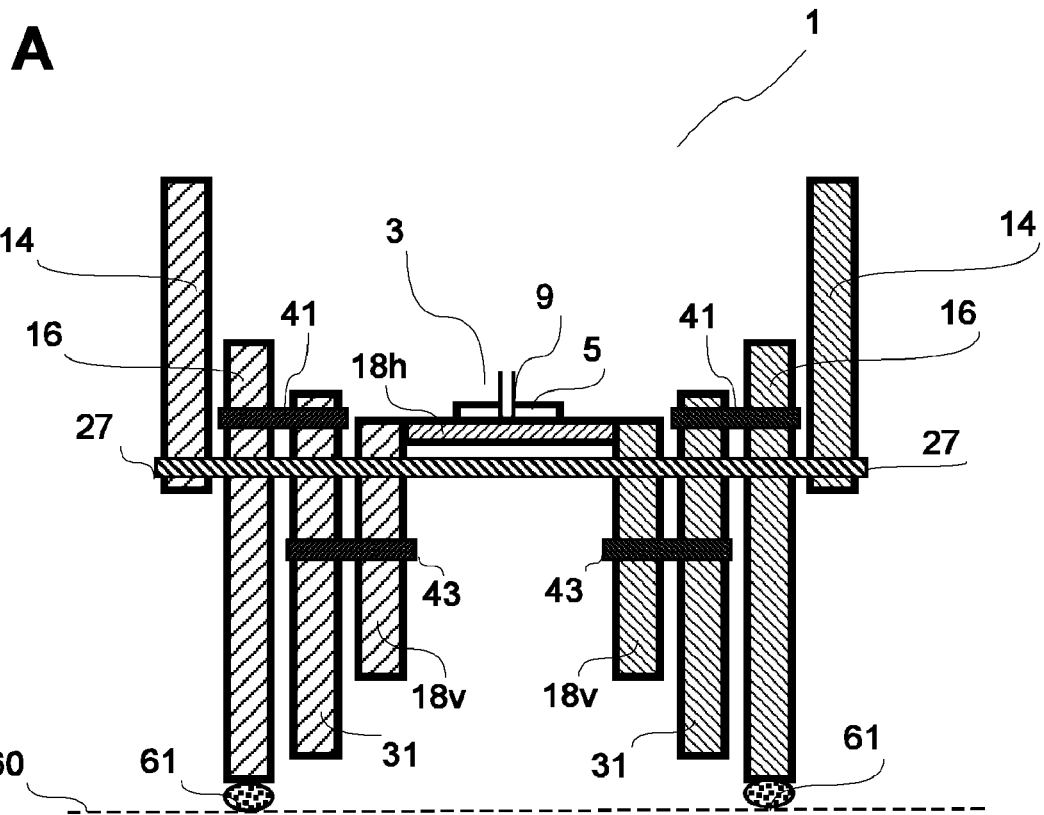
FIG. 6: Cross section of an embodiment of an insertion device with pivoting and guiding means. A: before insertion; B: cannula inserted.
Figure 6:
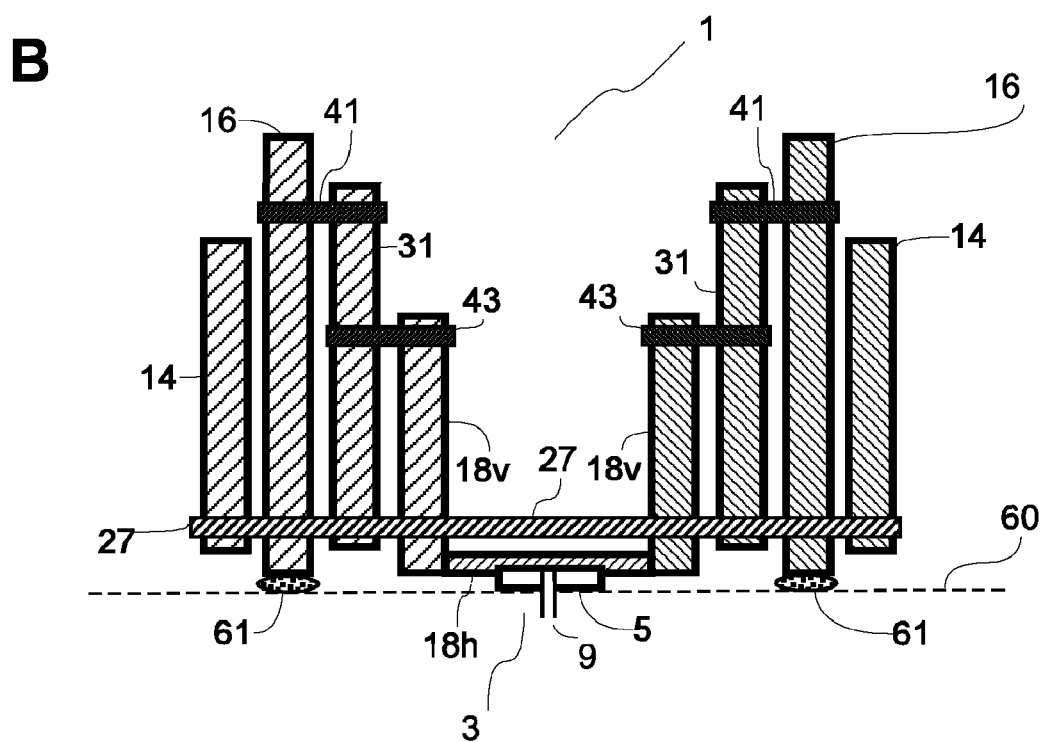

FIG. 6 shows a cross section of an embodiment of an insertion device 1 according to the invention for inserting a medical device 3. The cross section goes across penetrating member 9 and the length of rotating/pivoting shaft 27, an in direction of insertion, i.e. perpendicular to the surface 60 of the skin. The various shapes and dimensions, such as thickness and height are depicted schematically. In FIG. 6 A, the insertion device 1 is seen ready for application/insertion, with the medical device 3—comprising body 5 and penetration member 9—pointing upwards, i.e. away from the patient. The insertion device 1 comprises means for (i) providing a pivoting/rotating movement of the medical device 3, followed by (ii) a longitudinal movement of the medical device 3 into the direction of insertion of the penetrating member 9.

In one embodiment of the invention, the pivoting/rotating movement of the medical device 3 occurs together with a longitudinal movement in direction of insertion. In another embodiment of the invention, rotation means are provided, that provide a rotation/pivoting movement of the medical device 3, independently of a longitudinal movement of the medical device 3 in direction of insertion. In a further embodiment, rotation means are provided, that provide a rotation/pivoting of the medical device 3 from a start position, where the penetrating member 9 is not pointing into direction of insertion, to a second position, where the penetrating member 9 is pointing into the direction of insertion. This rotation/pivoting movement takes place, essentially without longitudinal movement of the medical device 3 into direction of insertion. After completion of rotation/pivoting movement, i.e. when the penetrating member 9 is aligned in insertion direction, insertion means provide a longitudinal insertion of the penetrating member 9 of the medical device.

In the embodiment illustrated in FIG. 6, said insertion device 1 comprises means for providing a pivoting/rotating movement of the medical device 3, as well as a longitudinal movement of the medical device 3. Said means comprise a top section 14 constituting a top part of the device in FIG. 6A i.e. when the device is positioned against the patients skin but before insertion, a lower section 16 constituting a lower part in FIG. 6A actually touching the patient's skin, a pivoting member 31, vertical device mounting means 18v, horizontal device mounting means 18h, a through-going shaft 27, a first pivoting shaft 41, and a second pivoting shaft 43. Lower section 16, pivoting member 31, and vertical device mounting means 18v comprise each a slot (16s, 31s and 18s, respectively), which are not shown in this Figure. The embodiment of the insertion device is symmetric across the axis defined by the direction of insertion, essentially perpendicular to the surface of the skin 60. Although not depicted as being part of one member, top sections 14 and lower sections 16 can be two separate pieces or parts of the same piece. Also the vertical device mounting means 18v can be two separate pieces or parts of the same piece. Furthermore, the vertical device mounting means 18v and the horizontal device mounting means 18h can comprise one, two or more pieces. In one embodiment, top section 14 and lower section 16 can be of cylindrical shape, similar to the embodiment depicted in FIG. 3. Through-going shaft 27 goes across and connects top section 14, lower section 16, pivoting member 31, and vertical device mounting means 18v. The first pivoting shaft 41 goes through lower section 16 and pivoting member 41. The second pivoting shaft 43 goes through pivoting member 41 and vertical device mounting means 18v. Attachment means for the respective shafts are not shown. In one embodiment, one or more rotating means are provided in order to allow rotation of one or more shafts. In another embodiment, one or more shafts are connected permanently to at least one member of the group comprising top section 14, lower section 16, pivoting member 31, or vertical device mounting means 18*v*. In the depicted embodiment the through-going shaft 27 and the first and second pivoting shafts 41 and 43 are parallel to each other, and perpendicular to top section 14, lower section 16, pivoting member 31 and vertical device mounting means 18*v*. In another embodiment, through-going shaft 27, first pivoting shaft 41 or second pivoting shaft 41 are not parallel to each other. In a further embodiment, at least one or more members selected from the group comprising top section 14, lower section 16, pivoting member 31 and vertical device mounting means 18*v* are not parallel to at least one other member of said group.

In this embodiment, the order of said means for providing a rotation as well as a longitudinal movement is (from the outside of the insertion device to the inside): top section 14, a lower section 16, a pivoting member 31, vertical device mounting means 18*v*, horizontal device mounting means 18*h*. In another embodiment, the order of said means can be different, and the, first and second pivoting shafts 41 and 43 may go through additional sections and or members, and/or through going shaft 27 may not go through all members listed above.

Furthermore, in the embodiment depicted in FIG. 6, the insertion device 1 comprises a soft member 61, which is attached at the lower end of lower section 16. The function of soft member 61 is to act as a buffer between the solid parts of the lower section 16 and the surface of the skin 60 of the patient, thereby reducing discomfort for the user. This buffer function can comprise a more uniform distribution of pressure, as well as reducing the discomfort for the patient, when experiencing a device that is colder than body temperature on the skin. In another embodiment of the invention, a soft member 61 can be absent.

In FIG. 6 B, the medical device 1 presented in FIG. 6 A is now shown in a position, where the medical device 3 has been applied to the patient, and the penetrating member 9, or a part of said penetrating member 9 has penetrated the surface of the skin 60 of the patient. It can be seen, that only lower section 16, pivoting member 31, as well as first and second pivoting shafts 41 and 43 are in essentially in the same position as in FIG. 6A. Device mounting means 18*v* and 18*h*, thus also medical device 3 have rotated 180° around through-going shaft 27. This is achieved by applying a force by pressing on top section 14, whereby a major fraction of this force is relayed to through-going shaft 27, which then induces a pivoting movement of the pivoting member 31 around the first pivoting shaft 41, thus inducing rotation of the device mounting means 18. Buffer member 61 is now shown in a compressed position, and the surface body 5 of the medical device 3 is in contact with the surface of the skin 60 of the patient.

Figure 7:
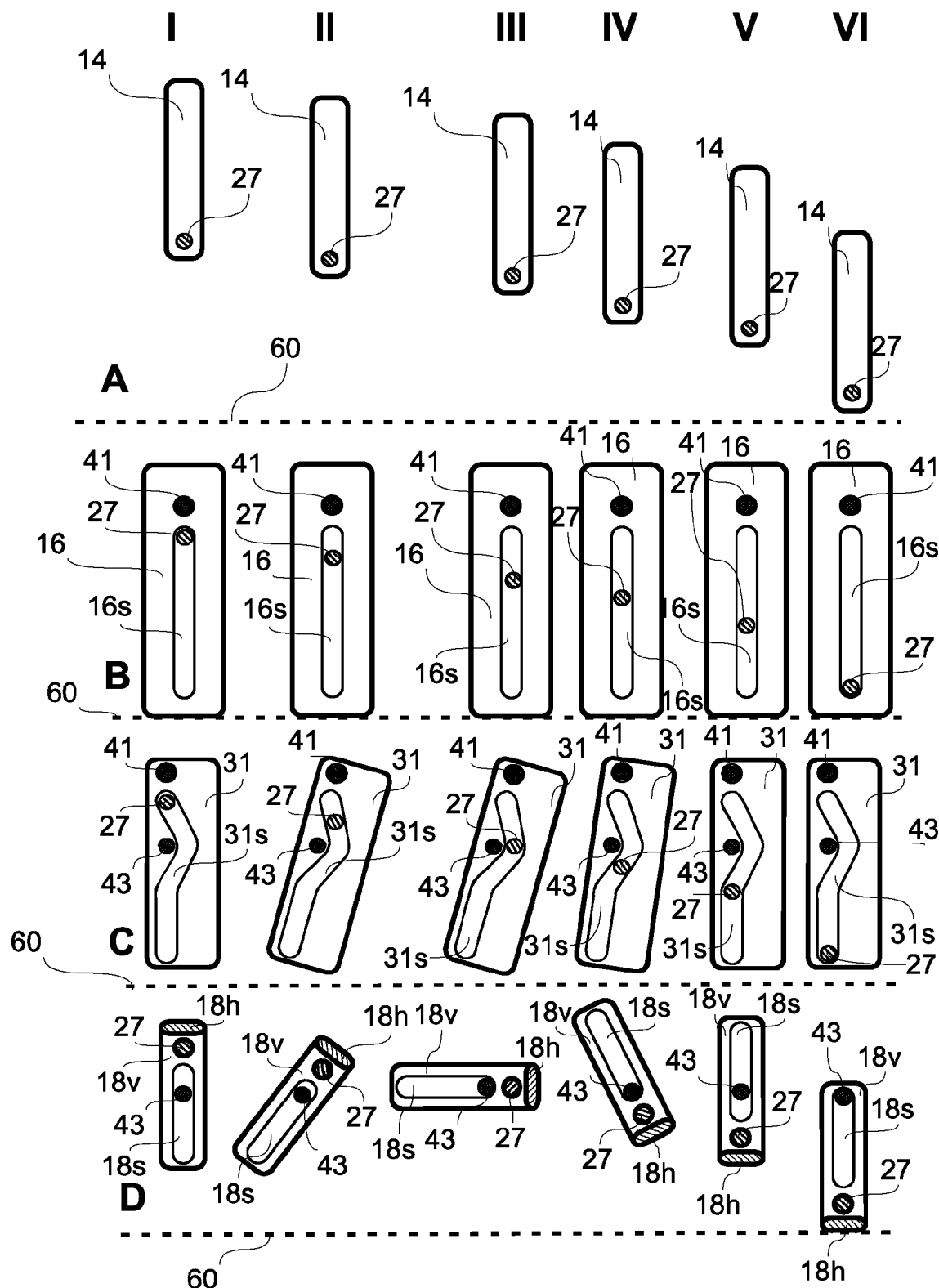
FIG. 7: Pivoting and guiding means and their relative positions during insertion (positions I-VI).
Figure 8:
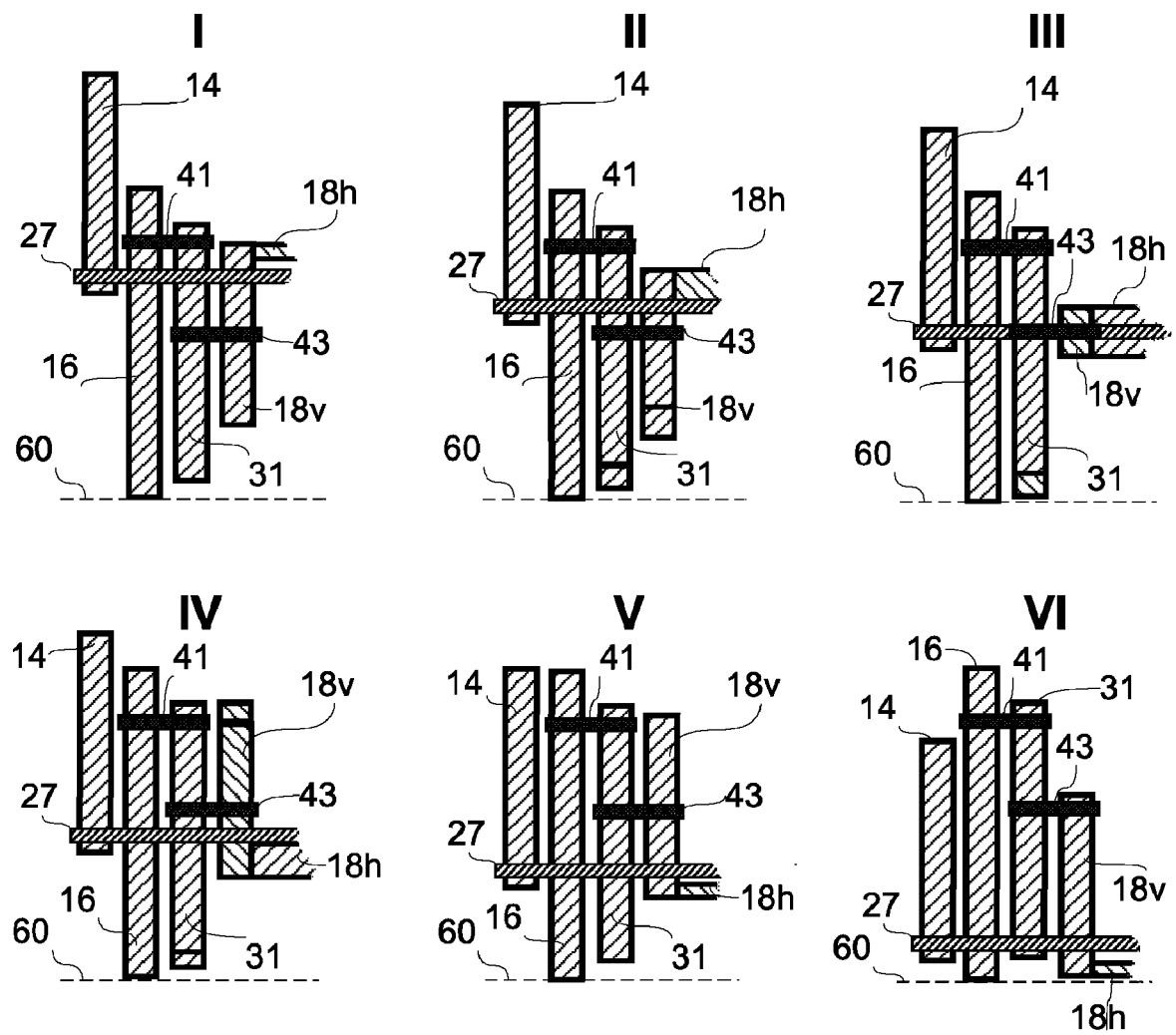
FIG. 8: Another view of pivoting and guiding means and their relative positions during insertion (positions I-VI).

The interactions leading to rotation and longitudinal movement of the device mounting means 18*h*, 18*v* and medical device 3 are described in more details in FIGS. 7 and 8, and the following section of the detailed description.

FIG. 7 shows another view of the means of the embodiment of and insertion device 1 presented in FIG. 6 (A: top section 14; B: lower section 16; C pivoting member 31; D: device mounting means 18*v* and 18*h*). Only a smaller portion of the horizontal device mounting means 18*h* is presented, and a medical device is not shown. The positions I-VI are:
I: start position;
II: ~45° rotation of device mounting means 18*v*, 18*h*;
III: ~90° rotation of device mounting means 18*v*, 18*h*;
IV: ~135° rotation of device mounting means 18*v*, 18*h*;
V: 180° rotation of device mounting means 18*v*, 18*h*;
VI: end position (inserted).

Positions I and VI correspond to the positions depicted in FIGS. 6 A and B, respectively. The direction of view is from the centre of the insertion device 1, and parallel with through-going shaft 27. The pivoting/rotating movements of the different members become apparent, and their respective distances from the skin surface 60 can be seen. Shapes and outer dimensions of the depicted means are selected arbitrarily for clarity. In a further embodiment, outer section 14 is provided with a handle (not shown), to facilitate application of the insertion device 1.

In FIG. 7A it becomes apparent, that by pushing top section 14 downwards, (i.e. in direction of insertion and the patient), through going shaft 27 is pushed down as well. In the depicted embodiment, top section 14 has an opening, as wide or wider as through going shaft 27. It is seen that the through-going shaft 27 is attached towards the lower end (i.e. the end facing the patient). In the depicted embodiment, the shaft is fixed. In another embodiment, it can rotate. Position I is the start position, in which outer section 14 is furthest away from the surface 60 of the patient. In position VI, outer section 14 is closest to the patient.

FIG. 7B shows that lower section 16 does not move, and that lower section 16 maintains in contact with surface 60 of the skin of a patient. Six positions of through-going shaft 27 within controlling slot 16*s* are seen (I-VI). Towards the upper end of the lower section 16, above the controlling slot 16*s*, an opening is provided for attaching the first pivoting shaft 41. In the depicted embodiment, the opening is wider than the diameter of the first pivoting shaft 41, and said first pivoting shaft 41 can rotate within said opening. In another embodiment, the first pivoting shaft 41 cannot rotate. In direction of insertion, a controlling slot 16*s* is provided parallel to the direction of insertion within lower section 16. Through-going shaft 27 is encompassed by said controlling slot 16*s*, and controls the length of movement of the top section 14, as top section 14 and through-going shaft 41 are attached. The length of the slot is longer than the length of insertion.

FIG. 7C shows that pivoting member 31 comprises a guiding slot 31*s*, in which through-going member 27 can move is up and down. Above guiding slot 31*s*, a first pivoting shaft 41 is provided, and pivoting member 31 can pivot/rotate around pivoting axis 41. In one embodiment, first pivoting shaft 41 is attached to lower section 16, and pivoting member 31 comprises an opening or bearing for pivoting axis 41. In another embodiment, first pivoting shaft 41 is attached pivoting member 31. Guiding slot 31*s* is straight, apart from a bended start section. Guiding slot 31*s* is sufficiently bended, so that a second pivoting shaft 43 can be provided, said second pivoting shaft 43 being positioned essentially in line between pivoting axis 41, the upper start point of guiding slot 31*s* and the straight lower section of guiding slot 31*s*. It becomes apparent that pushing outer section 41 downwards leads to a downwards movement of through-going shaft 27, guided longitudinally downwards by controlling slot 16*s* of the lower section 16. Pivoting member 31 is connected with the lower section 16 through the first pivoting shaft 41. The downwards movement of through-going shaft 27 leads to a pivoting movement of pivoting member 31 (position II), which reaches its maximum at position III, where the guiding slot 31*s* is most bend away from the straight line between start and end point of guiding slot 31*s*. A further downwards movement bottom leads to reduction of pivoting (position IV). When the through-going shaft reaches the straight lower section of guiding slot 31*s* and moves downwards, the pivoting movement of pivoting member 31 has stopped (position V-VI).

FIG. 7D shows the rotation and longitudinal movement of the horizontal and vertical device mounting means 18*h* and 18v from start position I to inserted position VI. The vertical device mounting means 18v point upwards in position I and downwards, i.e. towards the surface of the skin of a patient, in position V and VI. Horizontal device mounting means 18 comprise a longitudinal guiding slot 18s for second pivoting shaft 43, and an opening wide enough to encompass through-going shaft 27. Downwards movement of through-going shaft 27 provides a pivoting movement of pivoting member 31, thus also pivoting movement of the second pivoting shaft 43. In position II it is seen, that this in turn provides a rotation/pivoting movement of the horizontal and vertical device mounting means 18h and 18v. In position III, the vertical device mounting means 18v and 18h have turned approximately 90°, approximately 135° in position IV, and ~180° in positions V and VI. It becomes apparent the rate of turn is essentially determined by the angle between through-going shaft 27 and second pivoting shaft 43 (compare FIGS. 7 C and 7 D). The distances between through-going shaft 27 and second pivoting shaft 43 are varying during positions I to VI. The length of guiding slot 18s is longer than the length of insertion (difference between positions V and VI).

FIG. 8 shows a further view of the embodiment of an insertion device at the 6 different positions (I-VI) presented above in FIG. 7. The direction and view of the cross sections match the cross section presented in FIG. 6 A and FIG. 6 B, corresponding to positions I and VI in FIG. 7, respectively.

The invention claimed is:
1. An inserter device for inserting a penetrating member into the subcutaneous area or intramuscular area of a patient, said inserter device comprising:
a housing encompassing said penetrating member, said housing comprising a top section and a lower section;
a pivoting portion and a guiding member, the pivoting portion and the guiding member providing one or more pivoting movement(s) of the penetrating member from
a first position, where an insertion end of the penetrating member is not pointing into a direction of insertion, to
a second position, where the penetrating member is positioned within the housing and is aligned with the direction of insertion and at the second position the pivoting movement of the penetrating member stops, to
a third position, where the penetrating member protrudes from the housing and the penetrating member is aligned in the direction of insertion, the guiding member provides a straight longitudinal movement of the penetrating member from said second position to said third position.

2. An inserter device according to claim 1, wherein said pivoting portion and guiding members provide a fourth position by a straight longitudinal movement where the penetrating member is fully inserted in the patient, said straight longitudinal movement being of the same length or longer than the length of the penetrating member.

3. An inserter device according to claim 1, wherein said pivoting portion comprises at least one shaft and wherein the at least one shaft traverses the top section and the lower section.

4. An inserter device according to claim 3, wherein the at least one shaft consists of one through-going member or the at least one shaft consists of two or more pieces.

5. An inserter device according to claim 3, wherein a device mounting member is attached to the at least one shaft, and the device mounting member and the at least one shaft share the same center of rotation.

6. An inserter device according to claim 1, wherein said pivoting portion comprises one or more pivoting shafts and one or more pivoting members.

7. An inserter device according to claim 6, wherein a first pivoting shaft traverses the lower section and a pivoting member, and the first pivoting shaft is the center of rotation of said pivoting member.

8. An inserter device according to claim 7, wherein a second pivoting shaft traverses the pivoting member and a device mounting member.

9. An inserter device according to claim 6, wherein said guiding member comprises one or more rounded protrusions provided on a device mounting member, said protrusions extending away from the direction of insertion.

10. An inserter device according to claim 9, wherein said guiding member comprises a major protrusion flanked symmetrically by two minor protrusions, said major protrusion being aligned with the penetrating member along an axis extending perpendicular to the one or more pivoting shafts.

11. An inserter device according to claim 9, wherein the device comprises an upper guiding member and a lower guiding member, and said upper and lower guiding members are extending from an inner surface of the lower section and the interaction between the one or more rounded protrusions and the upper and lower guiding members provides a rotation of the penetrating member upon application of a downward force on the top section.

12. An inserter device according to claim 1, wherein said guiding member comprises one or more guiding slots.

13. An inserter device according to claim 12, wherein said one or more guiding slots are provided on the lower section, said one or more guiding slots being parallel to the direction of insertion, and being of the same length or longer than the length of said straight longitudinal movement and said one or more guiding slots encompassing a shaft, and restricting the length of the longitudinal movement of the shaft and the lower section.

14. An inserter device according to claim 12, wherein the one or more guiding slots are provided within a vertical section of a device mounting member, the one or more guiding slots are of the same length or longer than the length of said longitudinal movement, said one or more guiding slots encompassing a pivoting shaft, and restricting the movement of the second pivoting shaft.

15. An inserter device according to claim 1, wherein application of a downward force on the top section into the direction of insertion provides a rotation of the penetrating member through interactions of a shaft being guided by a guiding slot of the lower section and a guiding slot of a pivoting member, and through interactions of a first pivoting shaft and a second pivoting shaft being guided by the pivoting member and a guiding slot on a vertical section of a device mounting member.

16. An inserter device according to claim 1, wherein the penetrating member comprises an introducer needle extending at least partially through and supporting a medical device, and where the introducer needle is removed from the medical device after insertion of the penetrating member.

17. An inserter device according to claim 16, wherein said pivoting portion and guiding member provide a fifth position by a straight longitudinal movement, where the introducer needle is retracted through the medical device or into the housing.

18. An inserter device according to claim 17, where the medical device is a sensor, a port for injection of a fluid, or an infusion part.

19. An inserter device according to claim 1, wherein a central axis of insertion is parallel to a central axis of the insertion device.

20. An inserter device according to claim 1, wherein a central direction of insertion of the penetrating member is either essentially perpendicular to the patient's skin surface, or at an insertion angle of $0°<\alpha_{ins}<90°$.

21. An inserter device according to claim 1, wherein a center axis of the inserter device is essentially perpendicular to the patient's skin surface, or at an center angle of $0°<\alpha_{center}<90°$.

22. An inserter device according to claim 1, wherein the direction of insertion of the penetrating member is either parallel to a center axis of the inserter device, or at a deflection angle of $0°<\alpha_{defl}<90°$.

23. An inserter device for inserting a penetrating member into the subcutaneous area or intramuscular area of a patient, said inserter device comprising:
- a housing encompassing said penetrating member, said housing comprising a top section and a lower section;
- a pivoting portion; and
- a guiding member, the guiding member comprising one or more guiding slots, the pivoting portion and the guiding member providing one or more pivoting movement(s) of the penetrating member from
  - a first position, where an insertion end of the penetrating member is not pointing into a direction of insertion, to
  - a second position, where the penetrating member is positioned within the housing and is aligned with the direction of insertion and at the second position the pivoting movement of the penetrating member stops, to
  - a third position, where the penetrating member protrudes from the housing and the penetrating member is aligned in the direction of insertion, the guiding member provides a straight longitudinal movement of the penetrating member from said second position to said third position; and
- wherein the one or more guiding slots are provided within a pivoting member, said one or more guiding slots comprising a bent section towards an upper part of the pivoting member, and a straight section of the same length or longer than the length of said straight longitudinal movement, the one or more guiding slots encompassing a pivoting shaft, and restricting the movement of the pivoting shaft.

* * * * *